(12) United States Patent
Li et al.

(10) Patent No.: US 6,512,129 B1
(45) Date of Patent: Jan. 28, 2003

(54) EPOXIDATION PROCESS

(75) Inventors: Xiangmin Li, West Chester, PA (US); David W. Leyshon, West Chester, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/055,776

(22) Filed: Jan. 23, 2002

(51) Int. Cl.⁷ .............................................. C07D 301/19
(52) U.S. Cl. ....................................... 549/529; 549/530
(58) Field of Search ................................. 549/529, 530

(56) References Cited

U.S. PATENT DOCUMENTS

| | | | | |
|---|---|---|---|---|
| 3,351,635 A | 11/1967 | Kollar | ...................... | 260/348.5 |
| 4,066,706 A | 1/1978 | Schmidt | .................. | 260/610 B |
| 4,367,342 A | 1/1983 | Wulff et al. | ................. | 549/529 |
| 5,849,937 A | 12/1998 | Jubin, Jr. et al. | ............ | 549/529 |
| 5,883,268 A | 3/1999 | Lin et al. | ..................... | 549/529 |

*Primary Examiner*—Ba K. Trinh
(74) *Attorney, Agent, or Firm*—William C. Long

(57) ABSTRACT

Insoluble resinous sodium materials are separated from a hydroperoxide/olefin epoxidation feed by contact with a fine screen or a bed of coalescing solids.

7 Claims, 1 Drawing Sheet

EPOXIDATION PROCESS

BACKGROUND OF THE INVENTION

1. Field of the Invention

The present invention relates to the epoxidation of olefins such as propylene by reaction with an organic hydroperoxide using solid epoxidation catalyst and especially to a process wherein feed to the epoxidation has been treated with aqueous base, the improvement which comprises subjecting the epoxidation feed to a treatment prior to contact with the solid epoxidation catalyst to trap and remove insoluble materials which otherwise would adversely affect the epoxidation catalyst and reaction.

2. Description of the Prior Art

It is well known to form oxirane compounds such as propylene oxide by catalytic reaction of an olefin such as propylene with an organic hydroperoxide such as ethylbenzene hydroperoxide. The basic patent describing this technology is U.S. Pat. No. 3,351,635.

In one variant of the technology an insoluble solid heterogeneous catalyst is used to catalyze the epoxidation reaction. See, for example, U.S. Pat. No. 4,367,342. A patent illustrating procedures for carrying out this reaction is U.S. Pat. No. 5,849,937.

The organic hydroperoxide, e.g. ethylbenzene hydroperoxide, is advantageously formed by molecular oxygen oxidation of ethylbenzene. See, for example, U.S. Pat. No. 4,066,706.

It is advantageous, generally, to treat process streams such as the oxidate from the hydroperoxide forming step with basic materials in order to remove acidic components which otherwise would adversely affect the epoxidation. U.S. Pat. No. 5,883,268 is illustrative. The treated streams are usually washed thereafter in order to remove basic sodium materials.

A problem which arises, however, is that if the wash normally used to remove the sodium materials fails or if there is significant entrainment of sodium materials such as during a plant upset, these materials will enter the epoxidation reactor and plug and deactivate the catalyst bed. The problem is especially acute after the oxidate has been admixed with the olefin to be epoxidized. The solubility of resinous sodium containing materials is substantially lowered when the oxidate is mixed with olefin and the resulting insoluble resinous materials are prone to plug and deactivate the epoxidation catalyst bed unless first removed.

The present invention provides protection against such catalyst bed plugging and deactivation.

BRIEF DESCRIPTION OF THE INVENTION

In accordance with the present invention, the hydroperoxide and olefin feed admixture to the epoxidation reaction zone, wherein is contained solid epoxidation catalyst, is pretreated by passage through a screen or frit, or by passage through a bed of solid particles. As a result of this pretreatment, insoluble sodium containing resinous materials are trapped and separated from the epoxidation feed before the feed enters the epoxidation zone. Periodically, the screen or bed can be regenerated as by washing, or replaced.

DESCRIPTION OF THE DRAWING

The accompanying drawing illustrates the invention.

DETAILED DESCRIPTION

Figure 1:
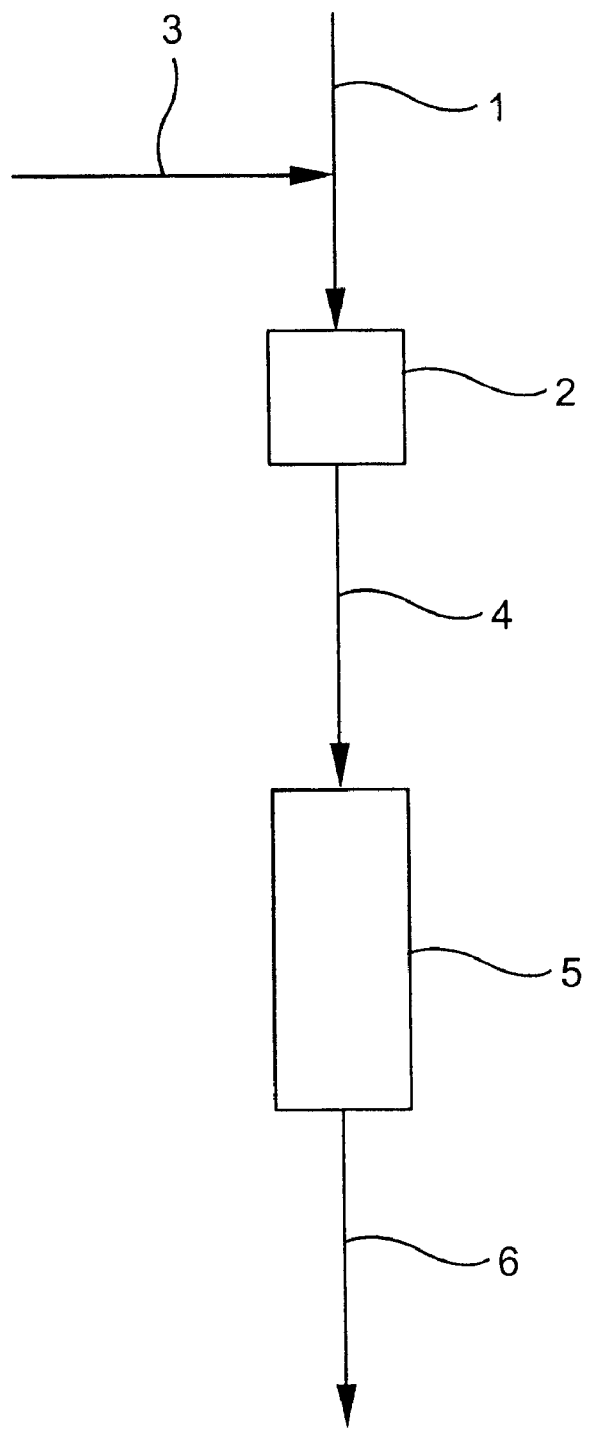

In carrying out the invention, the reactants, known reaction conditions and catalysts previously employed in hydroperoxide and epoxide production can be employed. Reference is made to the patents cited above, the disclosures of which are incorporated herein by reference.

Referring to the accompanying drawing as illustrative, an ethylbenzene hydroperoxide stream from ethylbenzene oxidation, which had been treated with aqueous sodium hydroxide, decanted and the organic phase water washed and decanted, passes via line 1 to contact zone 2. Propylene reactant passes via line 3 and is admixed with the ethylbenzene hydroperoxide stream before entry into contact zone 2.

During the aqueous caustic treatment of the ethylbenzene oxidate and decantation, there are formed various higher molecular weight sodium containing resinous materials which are separated by decantation from organic phase; normally the sodium containing materials are present in the organic hydroperoxide phase in only very small amounts, e.g. less than 1 ppm. During periods of upset, however, increased amounts of the sodium containing resinous materials, e.g. up to 15 ppm, are contained in the organic phase and when the oxidate is admixed with the olefin epoxidation reactant, the solubility of these sodium containing resinous materials is substantially reduced with the result that such resinous materials precipitate as solids in the oxidate/olefin hydrocarbon mixture. If the feed to the epoxidation zone contains such precipitated resinous materials, the result is deactivation and plugging of the catalyst bed. The resins are extremely sticky and tend to coat the solid catalyst particles as well as the reactor surfaces, soon incapacitating the epoxidation reaction zone. In addition to deactivating the catalyst, the deposition of such resinous materials causes a rapid rise in the pressure drop through the reaction zone and eventual plugging. It is important for successful and continued operation that the resinous materials be removed from the reactant stream prior to entry into the epoxidation zone.

Referring to the accompanying drawing, zone 2 is provided through which the epoxidation feed is passed. Under normal circumstances where the content of sodium materials is very low, there are essentially no insoluble sodium materials in the epoxidation feed and the feed passes through zone 2 without a substantial pressure drop increase. However, when the sodium material content increases to above about 3 ppm as sodium by weight based on oxidate, insolubles are formed and these are removed in zone 2. In one embodiment of the invention, zone 2 is packed with neutral or slightly basic particulate material such as silica which is effective to entrap and remove the insoluble resinous sodium materials. In a more preferred environment, zone 2 is provided with 1 or more fine mesh metal screens, illustratively of a 120 micron size or finer, which screens effectively entrap and remove the insoluble resinous materials from the reactor feed. Still another alternative is to provide in zone 2 a packed bed comprised of one or more metal frits, which are sintered metal filters, and which are also effective in entrapping and removing the resinous solids from the feed to the epoxidation zone. Other coalescing packing solids comprised of fibrous materials such as glass wool or steel wool can also be used.

The epoxidation feed now substantially free of contained insoluble resinous products passes from zone 2 via line 4 to epoxidation zone 5 wherein the ethylbenzene hydroperoxide and propylene contained therein contact a solid epoxidation catalyst and react to form propylene oxide. The reaction product mixture passes from zone 5 via line 6 and is worked up by known procedures to recover product propylene oxide.

The present invention is especially useful during periods of upset during the epoxidation plant operation. Under normal conditions, the content of the sodium containing resinous materials can be maintained sufficiently low, i.e. less than 1 ppm as sodium in oxidate, as not to cause significant problems in the epoxidation zone. However, during periods of plant upset there tend to be excessive concentrations of the resinous solids in the feed passing to the epoxidation zone and it is especially important that during these periods the sodium containing resinous solids be removed before the feed contacts the solid catalyst in order to prevent deactivation and/or plugging of the catalyst bed. Through practice of the invention, the catalyst bed is protected during periods when there is an excessive concentration of insoluble resins in the feed by entrapping and removing these materials in the manner herein described. The invention also provides timely warning of the malfunction of the caustic wash section, such that corrective measures can be taken before there are major operating problems.

The following are provided to illustrate the invention.

A commercial oxidate was prepared by the molecular oxygen oxidation of ethylbenzene to ethylbenzene hydroperoxide. The oxidate was washed with aqueous caustic and the organic phase was separated by decantation. The organic oxidate phase was comprised of about 35 wt % ethylbenzene hydroperoxide with the remainder essentially ethylbenzene. The sodium content was less than 1 ppm by weight as sodium based on oxidate.

The hydroperoxide stream was admixed with propylene in amount of about 3.5 parts by weight propylene per part of hydroperoxide and the resulting admixture was passed through a 25 micron stainless steel screen at a rate of 123 gal/min/ft$^2$ of screen area, the screen area including both metal and the actual opening.

During a two week run, the pressure drop upon passage through the screen gradually rose to about 2 psi and stabilized at that level.

Oxidate resulting from a period of plant upset was simulated by the addition of sodium benzoate in amount of about 5 ppm as sodium in oxidate.

When this feed was passed at the same rate through the same screen as above, in two hours the pressure drop had reached 5 psi and in five hours had reached 30 psi.

The above comparison demonstrates the effectiveness of the screen in retaining the various sodium materials as evidenced by the rapid pressure drop increase.

The simulated epoxidation feed containing sodium benzoate (5 ppm as sodium in oxidate) was tested with 10 micron metal frit at a feed rate of 9 gal/min/ft$^2$. Pressure drop rapidly increased reaching 20 psi in 1.25 hours which indicated successful insolubles separation.

The simulated epoxidation feed used above was tested using 10 micron, 25 micron and 36 micron stainless steel screens. In the following table, the times elapsed at various feed rates to reach 10 psi pressure drop are given:

TABLE 1

| Metal Screen | Feed rate (gal/min/ft$^2$) | Time to reach 10 psi $\Delta P$ |
| --- | --- | --- |
| 10 micron | 46 | 3.5 hr. |
| 25 micron | 46 | 4.8 hr. |
| 36 micron | 46 | 12.5 hr. |
| 25 micron | 46 | 4.8 hr. |
| 25 micron | 95 | 4 hr. |
| 25 micron | 123 | 3.3 hr. |

An additional advantage is that by conventional pressure drop monitoring means early plant upset detection can be achieved and remedial measures rapidly taken.

Generally, screens of 120 to 1100 mesh (Tyler Standard) are useful; these have screen openings of about 5 to 120 microns. Stainless steel is the preferred material of construction; other metals may have an adverse decomposing effect on the hydroperoxide.

Similarly, metal frits having mean pore diameters of 7 to 90 microns or packed beds having mean pore diameters of 7 to 90 microns can be used.

Other coalescing packings can also be employed including glass wool, metal meshes, and the like. Use of stainless steel screens is preferred since the screens are effective, relatively inexpensive and easily cleaned.

We claim:

1. In a process wherein an olefin and an organic hydroperoxide are admixed to form an admixture which is fed to an epoxidation zone and therein contacted with a solid epoxidation catalyst at conditions effective to form oxirane product, the feed admixture to the epoxidation zone containing insoluble resinous materials, the improvement which comprises separating the resinous materials before said admixture contacts the solid catalyst.

2. The process of claim 1 wherein the insoluble resinous materials are separated by passing the feed admixture through a fine metal screen.

3. The process of claim 2 wherein the metal screen has 5 to 120 micron openings.

4. The process of claim 1 wherein the insoluble resinous materials are separated by passing the feed through a packed bed of coalescing solids.

5. The process of claim 4 wherein said packed bed comprises one or more metal frits.

6. The process of claim 4 wherein said packed bed is a bed of fibrous material.

7. The process of claim 4 wherein said packed bed is a bed of glass wool.

* * * * *